(12) United States Patent
Sekiya et al.

(10) Patent No.: US 9,804,118 B2
(45) Date of Patent: Oct. 31, 2017

(54) GAS SENSOR

(71) Applicant: NGK Insulators, Ltd., Nagoya (JP)

(72) Inventors: Takayuki Sekiya, Nisshin (JP); Naoya Saito, Nagoya (JP); Shota Kageyama, Chita-gun (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 14/672,735

(22) Filed: Mar. 30, 2015

(65) Prior Publication Data

US 2015/0276659 A1 Oct. 1, 2015

(30) Foreign Application Priority Data

Mar. 31, 2014 (JP) .................. 2014-072928
Mar. 26, 2015 (JP) .................. 2015-063962

(51) Int. Cl.
| | |
|---|---|
| G01N 27/414 | (2006.01) |
| G01N 27/407 | (2006.01) |
| G01N 27/409 | (2006.01) |
| G01N 27/417 | (2006.01) |

(52) U.S. Cl.
CPC ....... G01N 27/4071 (2013.01); G01N 27/409 (2013.01); G01N 27/417 (2013.01)

(58) Field of Classification Search
None
See application file for complete search history.

(56) References Cited

U.S. PATENT DOCUMENTS

| | | | | |
|---|---|---|---|---|
| 4,289,802 A | * | 9/1981 | Micheli | .................. C03C 3/061 |
| | | | | 204/421 |
| 4,824,548 A | * | 4/1989 | Iino et al. | .......... G01N 27/4071 |
| | | | | 204/406 |
| 5,413,683 A | | 5/1995 | Murase et al. | |
| 5,672,811 A | | 9/1997 | Kato et al. | |

(Continued)

FOREIGN PATENT DOCUMENTS

| | | |
|---|---|---|
| EP | 0 797 094 A2 | 9/1997 |
| EP | 1 359 412 A1 | 11/2003 |

(Continued)

OTHER PUBLICATIONS

Extended European Search Report (Application No. 15161777.6) dated Aug. 26, 2015.

*Primary Examiner* — J. Christopher Ball
(74) *Attorney, Agent, or Firm* — Burr & Brown, PLLC

(57) ABSTRACT

In a sensor element, a reference gas regulation pump cell pumps in oxygen to the periphery of a reference electrode in which a reference gas is introduced, by the flow of a control current Ip3 between the reference electrode and an outer pump electrode located in a region exposed to a measurement-object gas. An average current density of the reference electrode under the flow of the control current Ip3 is higher than 0 $\mu A/mm^2$ and lower than 400 $\mu A/mm^2$. The average current density is preferably not higher than 170 $\mu A/mm^2$. An average value of the control current Ip3 is preferably higher than 1 $\mu A$. The outer pump electrode as a measurement-object gas side electrode of the reference gas regulation pump cell may be provided on an outer surface of a layered body (or more specifically, on a second solid electrolyte layer).

6 Claims, 5 Drawing Sheets

(56) References Cited

U.S. PATENT DOCUMENTS

| | | | | |
|---|---|---|---|---|
| 5,879,525 A | * | 3/1999 | Kato | G01N 27/419 |
| | | | | 204/424 |
| 2002/0070111 A1 | * | 6/2002 | Sugiyama | G01N 27/4071 |
| | | | | 204/429 |
| 2011/0147214 A1 | | 6/2011 | Fujita et al. | |
| 2014/0102170 A1 | | 4/2014 | Kato | |

FOREIGN PATENT DOCUMENTS

| | | |
|---|---|---|
| JP | 3798412 B | 7/2006 |
| JP | 2011-102797 A | 5/2011 |
| WO | 2013/005491 A1 | 1/2013 |

\* cited by examiner

GAS SENSOR

BACKGROUND OF THE INVENTION

1. Field of the Invention

The present invention relates to a gas sensor.

2. Description of the Related Art

A conventionally known gas sensor detects a specific gas concentration such as NOx in a gas to be measured or a measurement-object gas such as an exhaust gas of an automobile. For example, JP 3798412B and JP 2011-102797A describe gas sensors, each including a sensor element of a long plate-like shape formed by stacking a plurality of airtight oxygen ion-conductive solid electrolyte layers.

FIG. 6 is a sectional schematic diagram schematically illustrating one exemplary configuration of a prior art gas sensor 300. As illustrated, this gas sensor 300 includes a sensor element 307. The sensor element 307 is provided as an element of stacked structure by stacking oxygen ion-conductive dense solid electrolyte layers 301 to 306. In this sensor element 307, a measurement-object gas flowing portion in which measurement-object gas is introduced is formed between a lower surface of the solid electrolyte layer 306 and an upper surface of the solid electrolyte layer 304. The measurement-object gas flowing portion includes a gas inlet 310 and first to third internal cavities 320, 340 and 361. A measurement electrode 344 is formed on a lower surface of the third internal cavity 361 (upper surface of the solid electrolyte layer 304). An outer pump electrode 323 is formed on an upper surface of the solid electrolyte layer 306. A reference gas introducing space 343 which a reference gas used as a standard for detection of a specific gas concentration in the measurement-object gas is introduced in is formed between an upper surface of the solid electrolyte layer 303 and a lower surface of the solid electrolyte layer 305. A reference electrode 342 is formed on the upper surface of the solid electrolyte layer 303 facing the reference gas introducing space 343. The reference electrode 342 is covered by a reference gas introducing layer 348 made of a porous material, and the reference gas is introduced from the reference gas introducing space 343 through the reference gas introducing layer 348 into the reference electrode 342. In this gas sensor 300, when the measurement-object gas is introduced into the third internal cavity 361 of the measurement-object gas flowing portion, an electromotive force Va is generated between the measurement electrode 344 and the reference electrode 342. Oxygen is pumped in or pumped out via the outer pump electrode 323 and the measurement electrode 344, based on this electromotive force Va. The gas sensor 300 detects the specific gas concentration in the measurement-object gas, based on an electric current Ip2 during pump-in or pump-out.

CITATION LIST

Patent Literature

PTL 1: JP 3798412 B
PTL 2: JP 2011-102797 A

SUMMARY OF THE INVENTION

In the prior art gas sensor 300 shown in FIG. 6, a front (left in FIG. 6) region ahead of the sensor element 307 in which the gas inlet 310 is located is separated from a rear (right in FIG. 6) region in which the reference gas introducing space 343 is located by a sealing member or the like (not shown). When the pressure of the measurement-object gas is temporarily increased, the measurement-object gas may slightly enter the reference gas introducing space 343. This may temporarily decrease an oxygen concentration of the reference gas in the periphery of the reference electrode 342 and may thus affect the detection accuracy of the specific gas concentration. A possible countermeasure against this problem may pump in oxygen to the periphery of the reference electrode 342 by the flow of electric current between an electrode provided to be exposed to the measurement-object gas and the reference electrode. This compensates for reduction of the oxygen concentration when the measurement-object gas enters the reference gas introducing space 342. The long-time flow of electric current, however, causes deterioration of the reference electrode. This is likely to change the electromotive force between the measurement electrode 344 and the reference electrode 342 and fail to maintain a reference potential of the reference electrode.

By taking into account the problems described above, an object of the invention is to compensate for reduction of an oxygen concentration in the periphery of a reference electrode and further suppress a change of a reference potential in long time use.

The invention may be implemented by the following aspects, in order to achieve the above object.

According to one aspect of the invention, there is provided a gas sensor. The gas sensor may comprise a layered body formed by stacking a plurality of oxygen ion-conductive solid electrolyte layers and configured to provide a measurement-object gas flowing portion which a gas to be measured or a measurement-object gas is introduced and flowed in and a reference gas introducing space which a reference gas used as a standard for detection of a specific gas concentration in the measurement-object gas is introduced in; a reference electrode formed inside of the layered body and configured to receive the reference gas introduced therein via the reference gas introducing space; a measurement electrode provided on an inner peripheral surface of the measurement-object gas flowing portion; a measurement-object gas side electrode located in a region of the layered body that is exposed to the measurement-object gas; a detecting device configured to detect the specific gas concentration in the measurement-object gas, based on an electromotive force generated between the reference electrode and the measurement electrode; and a reference gas adjusting device configured to pump in oxygen to periphery of the reference electrode by a flow of control current between the reference electrode and the measurement-object gas side electrode. An average current density of the reference electrode under the flow of control current may be higher than 0 $\mu A/mm^2$ and lower than 400 $\mu A/mm^2$.

In the gas sensor of this aspect, oxygen is pumped in to the periphery of the reference electrode by the flow of control current between the reference electrode formed inside of the layered body and configured to receive the reference gas introduced therein and the measurement-object gas side electrode located in the region that is exposed to the measurement-object gas. This compensates for reduction of an oxygen concentration in the periphery of the reference electrode, for example, when the measurement-object gas enters the reference gas introducing space. The average current density of the reference electrode under the flow of control current is higher than 0 $\mu A/mm^2$ and is lower than 400 $\mu A/mm^2$. Controlling the average current density to be lower than 400 $\mu A/mm^2$ more effectively suppresses deterioration of the reference electrode due to the flow of electric current and thereby more effectively suppresses a change of the reference potential in long time use. Accordingly, this aspect compensates for reduction of the oxygen concentration in the periphery of the reference electrode, while suppressing a change of the reference potential in long time use. The "average current density" herein means a current density calculated by dividing an average value of control current by the area of the reference electrode. The "average value of control current" is a time-averaged value of an instantaneous value of control current with regard to an object period (for example, one period when the control current is periodic) when the control current is not constant. The reference gas adjusting device is not limited to the configuration of consistently pumping in oxygen to the periphery of the reference electrode but may employ a time period in which oxygen is pumped out from the periphery of the reference electrode to the periphery of the measurement-object gas side electrode. In this application, the requirement is that the overall moving direction of oxygen in a predetermined sufficiently long time should be the direction of pumping in oxygen from the periphery of the measurement-object gas side electrode toward the periphery of the reference electrode. In other words, the requirement is that the total pump-in amount of oxygen to the periphery of the reference electrode should be greater than the total pump-out amount of oxygen from the periphery of the reference electrode in the predetermined sufficiently long time.

In the gas sensor of the above aspect, the average current density may be not higher than 170 $\mu A/mm^2$. This enhances the effect of further suppressing a change of the reference potential in long time use.

In the gas sensor of the above aspect, an average value of the control current may be higher than 1 $\mu A$. It is thus unlikely that the effect of compensating for reduction of an oxygen concentration in the periphery of the reference electrode is insufficient.

In the gas sensor of the above aspect, the measurement-object gas side electrode may be provided on an outer surface of the layered body. For example, when the measurement-object gas side electrode is provided inside of the measurement-object gas flowing portion, oxygen in the measurement-object gas flowing portion is pumped into the reference electrode side. This may affect the detection accuracy. Providing the measurement-object gas side electrode not inside of the measurement-object gas flowing portion but on the outer surface suppresses such effect on the detection accuracy.

The gas sensor of the above aspect may further comprise an outer electrode provided on an outer surface of the layered body. The detecting device may pump out or pump in oxygen via the measurement electrode and the outer electrode based on an electromotive force produced between the reference electrode and the measurement electrode and may detect the specific gas concentration in the measurement-object gas based on an electric current during pump-in or pump-out. In one application of this aspect, the outer electrode may also serve as the measurement-object gas side electrode. This reduces the total number of electrodes, compared with an application that separately provides an outer electrode and a measurement-object gas side electrode.

The gas sensor of the above aspect may be a porous body formed to cover the reference electrode and to be exposed to the reference gas introducing space and may include a reference gas introducing layer configured to introduce the reference gas from the reference gas introducing space to the reference electrode. The reference gas introducing layer may be exposed to the reference gas introducing space only on the other end side of the layered body relative to the reference electrode.

DETAILED DESCRIPTION OF THE INVENTION

Figure 1:
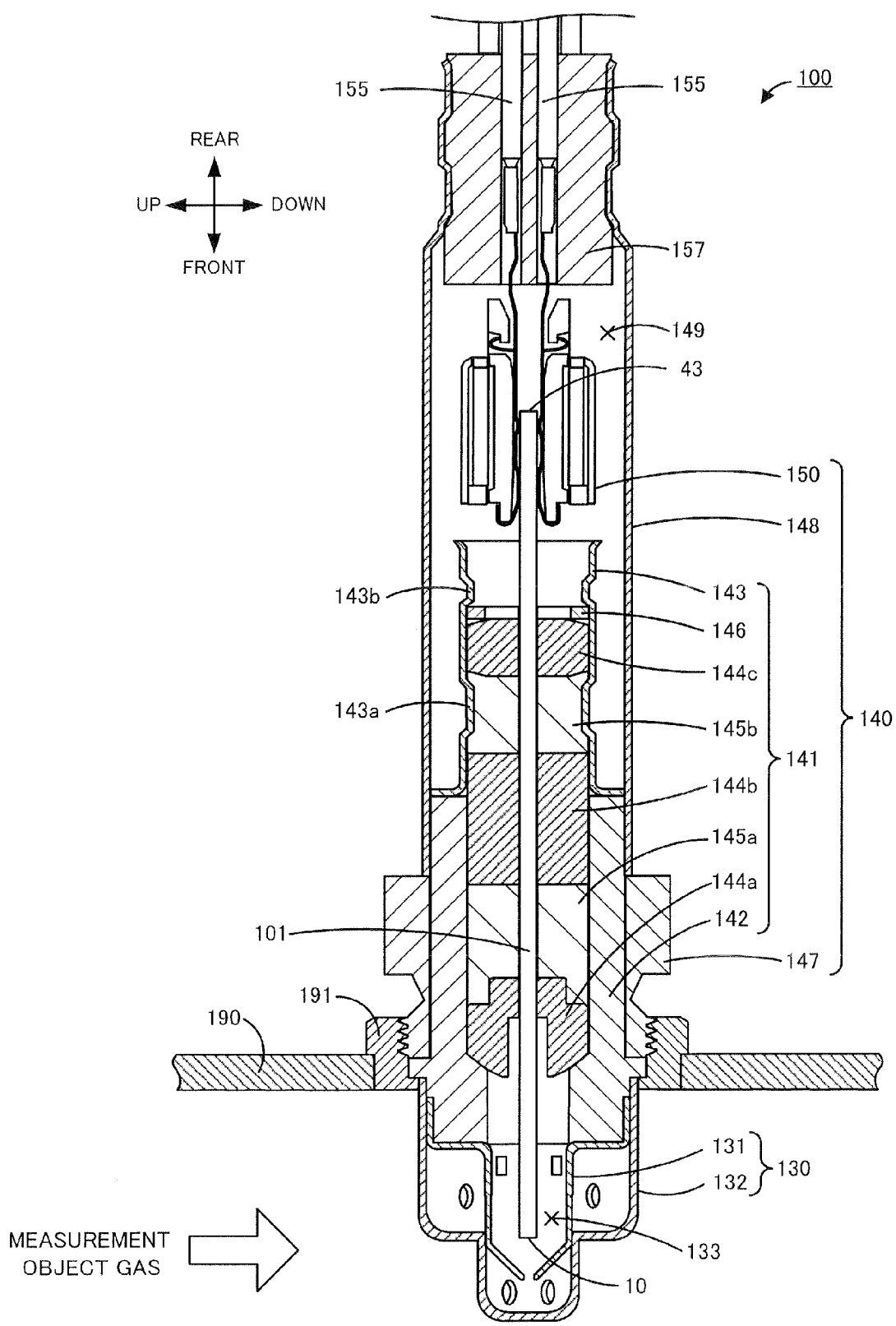
FIG. 1 is a vertical sectional view illustrating a gas sensor 100.
Figure 2:
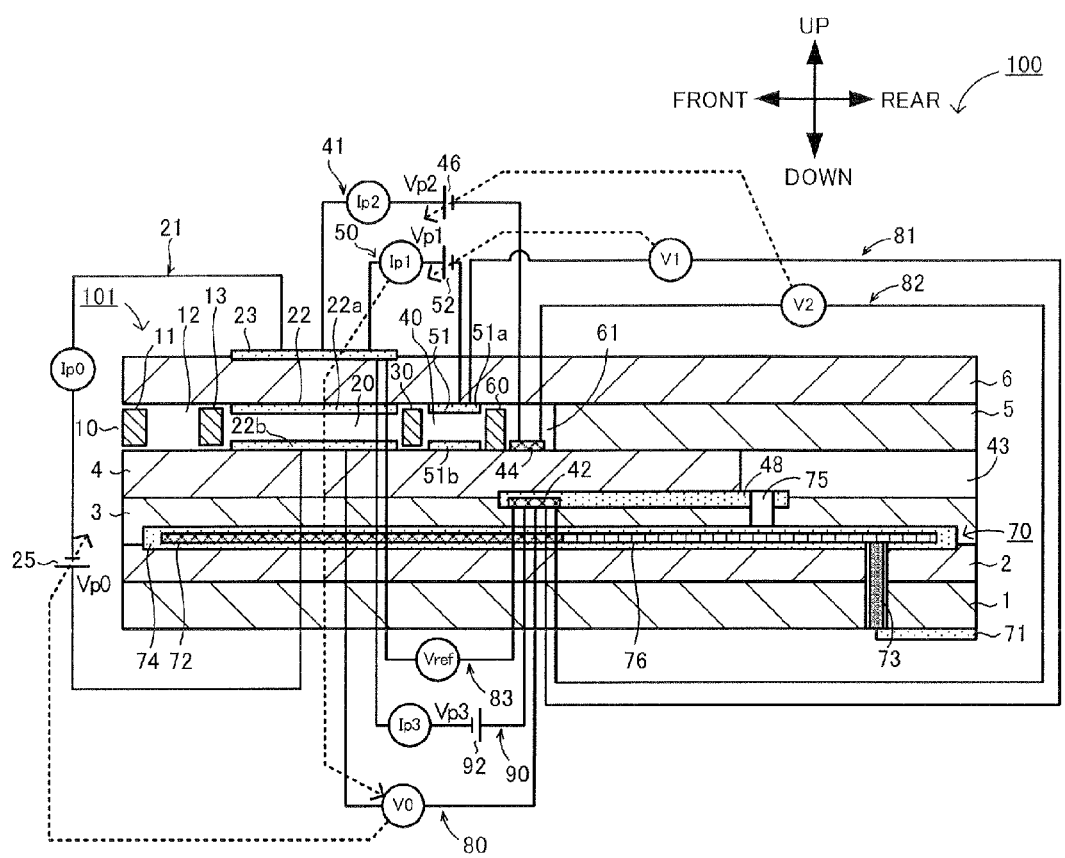
FIG. 2 is a sectional schematic diagram schematically illustrating one exemplified configuration of a sensor element 101.

The following describes an embodiment of the invention with reference to drawings. FIG. 1 is a vertical sectional view illustrating a gas sensor 100 according to one embodiment of the invention. FIG. 2 is a sectional schematic diagram schematically illustrating one exemplified configuration of a sensor element 101 included in the gas sensor 100. The sensor element 101 is in a long rectangular parallelepiped shape. In the description below, a longitudinal direction of the sensor element 101 (left-right direction in FIG. 2) is front-rear direction, and a thickness direction of the sensor element 101 (vertical direction in FIG. 2) is vertical direction. A width direction of the sensor element 101 (direction perpendicular to the front-rear direction and the vertical direction) is left-right direction. The configuration of the gas sensor shown in FIG. 1 is known and is described in, for example, WO 2013/005491A.

As shown in FIG. 1, the gas sensor 100 has the sensor element 101, a protective cover 130 configured to protect a front end side of the sensor element 101 and a sensor assembly 140 including a connector 150 that has continuity with the sensor element 101. This gas sensor 100 is mounted to, for example, a piping 190 such as an exhaust gas pipe of a vehicle as illustrated and is used to measure a specific gas concentration such as NOx or $O_2$ included in an exhaust gas which is a measurement-object gas or a gas to be measured. According to this embodiment, the gas sensor 100 is used to measure the NOx concentration as the specific gas concentration.

The protective cover 130 includes an inner protective cover 131 in a bottomed cylindrical shape to cover a front end of the sensor element 101 and an outer protective cover 132 in a bottomed cylindrical shape to cover the inner protective cover 131. The inner protective cover 131 and the outer protective cover 132 have a plurality of holes formed to flow the measurement-object gas inside of the protective cover 130. A sensor element chamber 133 is formed as a space surrounded by the inner protective cover 131. The front end of the sensor element 101 is placed in this sensor element chamber 133.

The sensor assembly 140 includes an element sealed body 141 in which the sensor element 101 is sealed and fixed, a nut 147 mounted to the element sealed body 141, an outer cylinder 148 and the connector 150 that comes into contact with and is electrically connected with electrodes (not shown) formed on surfaces (upper and lower surfaces) at a rear end of the sensor element 101.

The element sealed body 141 includes a main fitting 142 in a cylindrical shape, an inner cylinder 143 in a cylindrical shape coaxially welded and fixed to the main fitting 142, ceramic supporters 144a to 144c sealed in through holes inside of the main fitting 142 and the inner cylinder 143, green compacts 145a and 145b and a metal ring 146. The sensor element 101 is located on a center axis of the element sealed body 141 to pass through the element sealed body 141 in the front-rear direction. The inner cylinder 143 has a reduced diameter portion 143a formed to press the green compact 145b in a direction of the center axis of the inner cylinder 143, and a reduced diameter portion 143b formed to press forward the ceramic supporters 144a to 144c and the green compacts 145a and 145b via the metal ring 146. The pressing force from the reduced diameter portions 143a and 143b causes the green compacts 145a and 145b to be compressed between the main fitting 142 or the inner cylinder 143 and the sensor element 101. The green compacts 145a and 145b accordingly seal the sensor element chamber 133 in the protective cover 130 from a space 149 in the outer cylinder 148, while fixing the sensor element 101.

The nut 147 is coaxially fixed to the main fitting 142 and has a male threaded portion formed on its outer peripheral surface. The male threaded portion of the nut 147 is inserted into a fixation member 191 that is welded to the piping 190 and is formed to have a female threaded portion on its inner peripheral surface. The gas sensor 100 is accordingly fixed to the piping 190 in a state that the front end of the sensor element 101 and the protective cover 130 of the gas sensor 100 are protruded into the piping 190.

The outer cylinder 148 is provided to cover over the inner cylinder 143, the sensor element 101 and the connector 150. A plurality of lead wires 155 connected with the connector 150 are drawn outside from a rear end of the outer cylinder 148. The lead wires 155 are electrically connected with respective electrodes (described later) of the sensor element 101 via the connector 150. A clearance between the outer cylinder 148 and the lead wires 155 is sealed by a rubber plug 157. The space 149 in the outer cylinder 148 is filled with a reference gas (the air in the embodiment). The rear end of the sensor element 101 is placed in this space 149.

The sensor element 101 is an element of a layered body in which six layers respectively made of an oxygen ion-conductive solid electrolyte such as zirconia ($ZrO_2$) or more specifically a first substrate layer 1, a second substrate layer 2, a third substrate layer 3, a first solid electrolyte layer 4, a spacer layer 5 and a second solid electrolyte layer 6 are stacked in this sequence from a lower side of the drawing. The solid electrolyte forming these six layers is dense and air-tight. The sensor element 101 of this configuration may be manufactured, for example, by making ceramic green sheets corresponding to the respective layers subjected to specified processing and printing of a circuit pattern, stacking the processed green sheets and firing the stacked green sheets to be integrated.

A gas inlet port 10, a first diffusion controlling portion 11, a buffer space 12, a second diffusion controlling portion 13, a first internal cavity 20, a third diffusion controlling portion 30, a second internal cavity 40, a fourth diffusion controlling portion 60 and a third internal cavity 61 are formed to be adjacent to one another and communication with one another in this sequence and are provided on one end (left end in FIG. 2) of the sensor element 101 and between a lower surface of the second solid electrolyte layer 6 and an upper surface of the first solid electrolyte layer 4.

The gas inlet port 10, the buffer space 12, the first internal cavity 20, the second internal cavity 40 and the third internal cavity 61 are formed as internal spaces of the sensor element 101 by cutting out the spacer layer 5 to have an upper portion defined by the lower surface of the second solid electrolyte layer 6, a lower portion defined by the upper surface of the first solid electrolyte layer 4 and a side portion defined by a side surface of the spacer layer 5.

Each of the first diffusion controlling portion 11, the second diffusion controlling portion 13 and the third diffusion controlling portion 30 is provided in the form of two horizontally-long slits (where a longitudinal direction of their openings is a direction perpendicular to the sheet surface). The fourth diffusion controlling portion 60 is provided in the form of one horizontally-long slit (where a longitudinal direction of their openings is a direction perpendicular to the sheet surface) that is formed as a clearance from the lower surface of the second solid electrolyte layer 6. A region from the gas inlet port 10 to the third internal cavity 61 is also called measurement-object gas flowing portion.

A reference gas introducing space 43 is provided at a position that is farther from one end side than the measurement-object gas flowing portion and is located between an upper surface of the third substrate layer 3 and a lower surface of the spacer layer 5 to have a side portion defined by a side surface of the first solid electrolyte layer 4. For example, the air (atmosphere in the space 149 shown in FIG. 1) is introduced in the reference gas introducing space 43 as a reference gas for measurement of the NOx concentration.

An atmosphere introducing layer 48 is a layer made of a ceramic material such as porous alumina and exposed to the reference gas introducing space 43. The reference gas is introduced through the reference gas introducing space 43 into the atmosphere introducing layer 48. The atmosphere introducing layer 48 is formed to cover a reference electrode 42. The atmosphere introducing layer 48 applies a specified diffusion resistance to the reference gas in the reference gas introducing space 43 and introduces the resistance-applied reference gas into the reference electrode 42. The atmosphere introducing layer 48 is formed to be exposed to the reference gas introducing space 43 only on the rear end side (right side in FIG. 2) of the sensor element 101 relative to the reference electrode 42. In other words, the reference gas introducing space 43 is not formed to cover immediately above the reference electrode 42. The reference electrode 42 may, however, be formed immediately below the reference gas introducing space 43 shown in FIG. 2.

The reference electrode 42 is an electrode formed between the upper surface of the third substrate layer 3 and the first solid electrolyte layer 4. The atmosphere introducing layer 48 connecting with the reference gas introducing space 43 is provided in the vicinity of the reference electrode 42 as described above. The reference electrode 42 is formed directly on the upper surface of the third substrate layer 3, and a remaining part of the reference electrode 42 other than the part in contact with the upper surface of the third substrate layer 3 is covered by the atmosphere introducing layer 48. The oxygen concentrations (oxygen partial pressures) in the first internal cavity 20, in the second internal cavity 40 and in the third internal cavity 61 are measurable by using the reference electrode 42 as described later. The reference electrode 42 is formed as a porous cermet electrode (for example, cermet electrode of Pt and $ZrO_2$).

In the measurement-object gas flowing portion, the gas inlet port 10 is a region open to an external space and is arranged such that the measurement-object gas is taken from the external space through the gas inlet port 10 into the sensor element 101. The first diffusion controlling portion 11 is a region that applies a specified diffusion resistance to the measurement-object gas taken in from the gas inlet port 10. The buffer space 12 is a region provided to lead the measurement-object gas that is introduced from the first diffusion controlling portion 11, to the second diffusion controlling portion 13. The second diffusion controlling portion 13 is a region that applies a specified diffusion resistance to the measurement-object gas that is led from the buffer space 12 into the first internal cavity 20. In the course of introducing the measurement-object gas from outside of the sensor element 101 into the first internal cavity 20, the measurement-object gas rapidly taken from the gas inlet port 10 into the sensor element 101 by a pressure variation of the measurement-object gas in the external space (pulsation of exhaust gas pressure when the measurement-object gas is exhaust gas of an automobile) is not directly introduced into the first internal cavity 20 but is introduced into the first internal cavity 20 after cancellation of a concentration variation of the measurement-object gas through the first diffusion controlling portion 11, the buffer space 12 and the second diffusion controlling portion 13. This reduces the concentration variation of the measurement-object gas introduced into the first internal cavity 20 to a substantially negligible level. The first internal cavity 20 is provided as a space to regulate the oxygen partial pressure in the measurement-object gas introduced through the second diffusion controlling portion 13. The oxygen partial pressure is regulated by operation of a main pump cell 21.

The main pump cell 21 is an electrochemical pump cell, which includes an inner pump electrode 22 having a top electrode 22a provided over a substantially entire lower surface of the second solid electrolyte layer 6 facing the first internal cavity 20, an outer pump electrode 23 provided in an area corresponding to the top electrode 22a on an upper surface of the second solid electrolyte layer 6 to be exposed to an external space (sensor element chamber 133 shown in FIG. 1), and the second solid electrolyte layer 6 placed between these electrodes 22 and 23.

The inner pump electrode 22 is formed across the upper and lower solid electrolyte layers (second solid electrolyte layer 6 and first solid electrolyte layer 4) defining the first internal cavity 20 and the spacer layer 5 forming the side wall. More specifically, the top electrode 22a is formed on the lower surface of the second solid electrolyte layer 6 that forms a top surface of the first internal cavity 20. A bottom electrode 22b is formed directly on the upper surface of the first solid electrolyte layer 4 that forms a bottom surface of the first internal cavity 20. Side electrodes (not shown) are formed on side wall surfaces (inner surfaces) of the spacer layer 5 that form both side walls of the first internal cavity 20, such as to connect the top electrode 22a with the bottom electrode 22b and provide a tunnel-like structure.

The inner pump electrode 22 and the outer pump electrode 23 are formed as porous cermet electrodes (for example, cermet electrodes of Pt and $ZrO_2$ containing 1% Au). The inner pump electrode 22 exposed to the measurement-object gas is made of a material having the decreased reducing ability with regard to the NOx component in the measurement-object gas.

The main pump cell 21 serves to pump out oxygen from the first internal cavity 20 to the external space or pump in oxygen from the external space to the first internal cavity 20 by applying a desired pump voltage Vp0 between the inner pump electrode 22 and the outer pump electrode 23 and making a pump current Ip0 flow in either a positive direction or a negative direction between the inner pump electrode 22 and the outer pump electrode 23.

In order to detect the oxygen concentration (oxygen partial pressure) in the atmosphere of the first internal cavity 20, the inner pump electrode 22, the second solid electrolyte layer 6, the spacer layer 5, the first solid electrolyte layer 4 and the reference electrode 42 constitute an electrochemical sensor cell or more specifically a main pump-controlling oxygen partial pressure detection sensor cell 80.

The oxygen concentration (oxygen partial pressure) in the first internal cavity 20 is determined by measuring an electromotive force V0 in the main pump-controlling oxygen partial pressure detection sensor cell 80. The pump current Ip0 is controlled by feedback control of the pump voltage Vp0 of a variable power supply 25 to keep the electromotive force V0 constant. This maintains the oxygen concentration in the first internal cavity 20 at a specified constant value.

The third diffusion controlling portion 30 is a region that applies a specified diffusion resistance to the measurement-object gas with the oxygen concentration (oxygen partial pressure) controlled by operation of the main pump cell 21 in the first internal cavity 20 and leads the resistance-applied measurement-object gas to the second internal cavity 40.

The second internal cavity 40 is provided as a space to further regulate the oxygen partial pressure by means of an auxiliary pump cell 50 with respect to the measurement-object gas introduced through the third diffusion controlling portion 30 after regulation of the oxygen concentration (oxygen partial pressure) in the first internal cavity 20. This maintains the oxygen concentration in the second internal cavity 40 constant with high accuracy and thus enables the gas sensor 100 to measure the NOx concentration with high accuracy.

The auxiliary pump cell 50 is an auxiliary electrochemical pump cell, which includes an auxiliary pump electrode 51 having a top electrode 51a provided over a substantially entire lower surface of the second solid electrolyte layer 6 facing the second internal cavity 40, the outer pump electrode 23 (or any appropriate electrode outside of the sensor element 101 in place of the outer pump electrode 23) and the second solid electrolyte layer 6.

The auxiliary pump electrode 51 is provided to have a tunnel-like structure like the inner pump electrode 22 provided in the first internal cavity 20 and is placed in the second internal cavity 40. More specifically, the top electrode 51a is formed on the second solid electrolyte layer 6 that forms a top surface of the second internal cavity 40. A bottom electrode 51b is formed directly on the upper surface of the first solid electrolyte layer 4 that forms a bottom surface of the second internal cavity 40. Side electrodes (not shown) are formed on side wall surfaces (inner surfaces) of the spacer layer 5 that form both side walls of the second internal cavity 40, such as to connect the top electrode 51a with the bottom electrode 51b and provide a tunnel-like structure. Like the inner pump electrode 22, the auxiliary pump electrode 51 is made of a material having the decreased reducing ability with regard to the NOx component in the measurement-object gas.

The auxiliary pump cell 50 serves to pump out oxygen in the atmosphere from the second internal cavity 40 to the external space or pump in oxygen from the external space to the second internal cavity 40 by applying a desired voltage Vp1 between the auxiliary pump electrode 51 and the outer pump electrode 23.

In order to detect the oxygen partial pressure in the atmosphere of the second internal cavity 40, the auxiliary pump electrode 51, the reference electrode 42, the second solid electrolyte layer 6, the spacer layer 5 and the first solid electrolyte layer 4 constitute an electrochemical sensor cell or more specifically an auxiliary pump-controlling oxygen partial pressure detection sensor cell 81.

The auxiliary pump cell 50 performs pumping at a variable power supply 52 under voltage control based on an electromotive force V1 detected by this auxiliary pump-controlling oxygen partial pressure detection sensor cell 81. This controls the oxygen partial pressure in the atmosphere of the second internal cavity 40 to such a low partial pressure that substantially does not affect the measurement of NOx.

Additionally, its pump current Ip1 is used to control the electromotive force of the main pump-controlling oxygen partial pressure detection sensor cell 80. More specifically, the pump current Ip1 is input as a control signal into the main pump-controlling oxygen partial pressure detection sensor cell 80 to control its electromotive force V0. This control maintains a constant slope of the oxygen partial pressure in the measurement-object gas that is introduced from the third diffusion controlling portion 30 into the second internal cavity 40. In an application that the gas sensor 100 is used as an NOx sensor, the oxygen concentration in the second internal cavity 40 is maintained at a constant level of approximately 0.001 ppm by the operation of the main pump cell 21 and the auxiliary pump cell 50.

The fourth diffusion controlling portion 60 is a region that applies a specified diffusion resistance to the measurement-object gas with the oxygen concentration (oxygen partial pressure) controlled by operation of the auxiliary pump cell 50 in the second internal cavity 40 and leads the resistance-applied measurement-object gas to the third internal cavity 61. The fourth diffusion controlling portion 60 serves to control the amount of NOx flowing into the third internal cavity 61.

The third internal cavity 61 is provided as a space to further process the measurement-object gas introduced through the fourth diffusion controlling portion 60 after regulation of the oxygen concentration (oxygen partial pressure) in the second internal cavity 40 for the purpose of measurement of concentration of nitrogen oxides (NOx) in the measurement-object gas. Measurement of the NOx concentration is mainly performed in the third internal cavity 61 by operation of a measurement pump cell 41.

The measurement pump cell 41 measures the NOx concentration in the measurement-object gas in the third internal cavity 61. The measurement pump cell 41 is an electrochemical pump cell, which includes a measurement electrode 44 provided directly on an upper surface of the first solid electrolyte layer 4 facing the third internal cavity 61, the outer pump electrode 23, the second solid electrolyte layer 6, the spacer layer 5 and the first solid electrolyte layer 4. The measurement electrode 44 is a porous cermet electrode. The measurement electrode 44 also serves as a NOx reducing catalyst to reduce NOx present in the atmosphere of the third internal cavity 61.

The measurement pump cell 41 serves to pump out oxygen produced by degradation of nitrogen oxides in the ambient atmosphere of the measurement electrode 44 and detect the production amount of oxygen as a pump current Ip2.

In order to detect the oxygen partial pressure in the periphery of the measurement electrode 44, the first solid electrolyte layer 4, the measurement electrode 44 and the reference electrode 42 constitute an electrochemical sensor cell or more specifically a measurement pump-controlling oxygen partial pressure detection sensor cell 82. A variable power supply 46 is controlled based on an electromotive force V2 detected by the measurement pump-controlling oxygen partial pressure detection sensor cell 82.

The measurement-object gas introduced into the second internal cavity 40 passes through the fourth diffusion controlling portion 60 under control of the oxygen partial pressure and reaches the measurement electrode 44 in the third internal cavity 61. Nitrogen oxides in the measurement-object gas in the periphery of the measurement electrode 44 are reduced to produce oxygen ($2NO \rightarrow N_2 + O_2$). The produced oxygen is subjected to pumping by the measurement pump cell 41. In this process, a voltage Vp2 of the variable power supply 46 is controlled to maintain constant the control voltage V2 detected by the measurement pump-controlling oxygen partial pressure detection sensor cell 82. The amount of oxygen produced in the periphery of the measurement electrode 44 is proportional to the concentration of nitrogen oxides in the measurement-object gas. The concentration of nitrogen oxides in the measurement-object gas is thus calculated by using the pump current Ip2 of the measurement pump cell 41.

The second solid electrolyte layer 6, the spacer layer 5, the first solid electrolyte layer 4, the third substrate layer 3, the outer pump electrode 23 and the reference electrode 42 constitute an electrochemical sensor cell 83. The oxygen partial pressure in the measurement-object gas outside of the sensor is detectable by using an electromotive force Vref obtained by this sensor cell 83.

Additionally, the second solid electrolyte layer 6, the spacer layer 5, the first solid electrolyte layer 4, the third substrate layer 3, the outer pump electrode 23 and the reference electrode 42 constitute an electrochemical reference gas regulation pump cell 90. The reference gas regulation pump cell 90 performs pumping by means of a control current Ip3 flowed by using a voltage Vp3 applied by a variable power supply 92 connected between the outer pump electrode 23 and the reference electrode 42. The reference gas regulation pump cell 90 accordingly pumps in oxygen from an ambient space of the outer pump electrode 23 (sensor element chamber 133 shown in FIG. 1) to an ambient space of the reference electrode 42 (atmosphere introducing layer 48). The voltage Vp3 of the variable power supply 92 is determined in advance as a dc voltage to provide a specific value of the control current Ip3 (dc current of a constant value).

In the reference gas regulation pump cell 90, the area of the reference electrode 42, the control current Ip3 and the voltage Vp3 of the variable power supply 92 are determined in advance to control an average current density of the reference electrode 42 under the flow of the control current Ip3 to be higher than 0 $\mu A/mm^2$ and lower than 400 $\mu A/mm^2$. The average current density herein means a current density calculated by dividing an average value of the control current Ip3 by an area S of the reference electrode 42. The area S of the reference electrode 42 denotes an area of a part of the reference electrode 42 facing the atmosphere introducing layer 48 and is equal to an area (length in the front-rear direction ×width in the left-side direction) of a upper surface of the reference electrode 42 according to this embodiment. The thickness in the vertical direction of the reference electrode 42 is significantly smaller than the length in the front-rear direction and the width in the left-right direction of the reference electrode 42, so that the areas of side surfaces (front, rear, left and right surfaces) of the reference electrode 42 are negligible. The average value of control current is a time-averaged value with regard to a predetermined sufficiently long time in which an instantaneous change of the control current is negligible. The average current density is preferably not higher than 200 $\mu A/mm^2$, is more preferably not higher than 170 $\mu A/mm^2$ and is furthermore preferably not higher than 160 $\mu A/mm^2$. The area S of the reference electrode 42 is preferably not greater than 5 $mm^2$. The length in the front-rear direction and the width in the left-right direction of the reference electrode 42 are not specifically limited, but the length in the front-rear direction may be, for example, 0.2 to 2 mm, and the width in the left-right direction may be, for example, 0.2 to 2.5 mm. The average value of control current is, for example, 1 to 100 $\mu A$. The average value of control current is preferably higher than 1 $\mu A$, is more preferably not lower than 4 $\mu A$, is furthermore preferably not lower than 5 $\mu A$ and is especially preferably not lower than 8 $\mu A$.

In the gas sensor 100 of the above configuration, the measurement pump cell 41 receives the measurement-object gas with the oxygen partial pressure maintained at a constant low value (value that does not substantially affect the measurement of NOx) by the operation of the main pump cell 21 and the auxiliary pump cell 50. Accordingly, the NOx concentration in the measurement-object gas is determinable, based on the pump current Ip2 flowed by the measurement pump cell 41 pumping out oxygen produced by reduction of NOx approximately in proportion to the concentration of NOx in the measurement-object gas.

Additionally, the sensor element 101 is provided with a heater unit 70 serving as a temperature adjusting device to heat the sensor element 101 and keep the sensor element 101 warm, in order to enhance the oxygen ion conductivity of the solid electrolyte. The heater unit 70 includes a heater connector electrode 71, a heater 72, a through hole 73, a heater insulating layer 74, a pressure release hole 75 and a lead wire 76.

The heater connector electrode 71 is an electrode formed to be in contact with a lower surface of the first substrate layer 1. Connecting the heater connector electrode 71 with an external power supply allows for external power feeding to the heater unit 70.

The heater 72 is an electric resistor formed to be placed between the second substrate layer 2 and the third substrate layer 3. The heater 72 is connected with the heater connector electrode 71 via the lead wire 76 and the through hole 73 and generates heat by external power feeding through the heater connector electrode 71 to heat the solid electrolyte included in the sensor element 101 and keep the solid electrolyte warm.

The heater 72 is embedded over an entire area from the first internal cavity 20 to the third internal cavity 61 and serves to regulate the entire sensor element 101 to a temperature at which the solid electrolyte is activated.

The heater insulating layer 74 is an insulating layer of porous alumina formed from an insulating material such as alumina on upper and lower surfaces of the heater 72. The heater insulating layer 74 is formed to provide electrical insulation between the second substrate layer 2 and the heater 72 and electrical insulation between the third substrate layer 3 and the heater 72.

The pressure release hole 75 is a region provided to pass through the third substrate layer 3 and communicate with the reference gas introducing space 43 and is formed to relieve an increase in internal pressure accompanied with a temperature rise in the heater insulating layer 74.

The variable power supplies 25, 46, 52 and 92 shown in FIG. 2 are actually connected with the respective electrodes via lead wires (not shown) formed in the sensor element 101 and the connector 150 and the lead wires 155 shown in FIG. 1.

The following describes one exemplified procedure of manufacturing the gas sensor 100. The procedure first provides six unfired ceramic green sheets, each containing an oxygen ion-conductive solid electrolyte such as zirconia as the ceramic component. A plurality of sheet holes used for positioning in printing or in stacking and a plurality of required through holes are formed in the respective green sheets. A space forming the measurement-object gas flowing portion is provided in advance by, for example, punching in the green sheet for the spacer layer 5. The procedure subsequently performs a pattern printing process and a drying process to form various patterns in the respective ceramic green sheets respectively corresponding to the first substrate layer 1, the second substrate layer 2, the third substrate layer 3, the first solid electrolyte layer 4, the spacer layer 5 and the second solid electrolyte layer 6. More specifically, the patterns formed include, for example, the respective electrodes described above, lead wires connecting with the respective electrodes, the atmosphere introducing layer 48 and the heater unit 70. The pattern printing process may apply pattern-forming paste provided according to the properties required for each object on the green sheet by a known screen printing technique. The drying process may employ any known drying means. On completion of pattern printing and drying, the procedure performs a printing and drying process to print and dry an adhesive paste for stacking and bonding the green sheets corresponding to the respective layers. The procedure then performs a press bonding process to position the respective green sheets with the adhesive paste by aligning the sheet holes, stack the respective green sheets in a predetermined sequence and pressure bond the respective green sheets under predetermined temperature and pressure conditions to form one layered body. The resulting layered body includes a plurality of sensor elements 101. The layered body is cut into the size of the sensor elements 101. Each of the cut-out piece of the layered body is fired at a predetermined firing temperature to provide the sensor element 101.

After obtaining the sensor element 101, the procedure produces a sensor assembly 140 (shown in FIG. 1) with the sensor element 101 built therein and mounts the components such as the protective cover 130 and the rubber plug 157 to the sensor assembly 140 to complete the gas sensor 100. This manufacturing method of the gas sensor is known in the art and is described in, for example, WO 2013/005491.

The following describes the functions of the reference gas regulation pump cell 90 in detail. The measurement-object gas is introduced from the sensor element chamber 133 shown in FIG. 1 to the measurement-object gas flowing portion of the sensor element 101 including, for example, the gas inlet port 10. The reference gas (atmosphere) in the space 149 shown in FIG. 1 is, on the other hand, introduced into the reference gas introducing space 43 of the sensor element 101. The sensor element chamber 133 and the space 149 are separated from each other by the sensor assembly 140 (or more specifically, the green compacts 145a and 145b) and are sealed to prevent the gas flows therebetween. When the pressure of the measurement-object gas is temporarily increased, however, the measurement-object gas may slightly enter the space 149 via a clearance between the green compact 145*a* or 145*b* and the sensor element 101 or the main fitting 142. This causes a temporary decrease of the oxygen concentration in the periphery of the reference electrode 42 and thereby results in changing the reference potential that is the potential of the reference electrode 42. This may change an electromotive force on the basis of the reference electrode 42, for example, the electromotive force V2 of the measurement pump-controlling oxygen partial pressure detection sensor cell 82 and decrease the detection accuracy of the NOx concentration in the measurement-object gas. The reference gas regulation pump cell 90 serves to suppress such a decrease of the detection accuracy. The reference gas regulation pump cell 90 pumps in a fixed amount of oxygen from the sensor element chamber 133 to the space 149 by the flow of the control current Ip3. This compensates for reduction of oxygen and suppresses a decrease of the detection accuracy of the NOx concentration when the measurement-object gas has a temporary decrease of the oxygen concentration in the periphery of the reference electrode 42. The value of the control current Ip3 (for example, average value) may be determined experimentally or otherwise in advance, based on an expected decrease of the oxygen concentration in the periphery of the reference electrode 42 at an expected maximum value of the pressure of the measurement-object gas (i.e., an amount of oxygen to be pumped in to the periphery of the reference electrode 42).

In this embodiment, the control current Ip3 is consistently flowed during detection of the NOx concentration by the gas sensor 100, irrespective of whether the measurement-object gas slightly enters the space 149 or not. In this case, the reference gas regulation pump cell 90 pumps in oxygen to the periphery of the reference electrode 42 even when the oxygen concentration of the reference gas is not reduced in the periphery of the reference electrode 42, for example, when the measurement-object gas has relatively low pressure and does not enter the space 149. The excessive oxygen is, however, quickly diffused through the atmosphere introducing layer 48 to the reference gas introducing space 43 and the space 149. This accordingly prevents the oxygen concentration in the periphery of the reference electrode 42 from being excessively increased to decrease the detection accuracy of the NOx concentration.

In the process that the sensor cell 83 obtains (measures) the electromotive force Vref and detects the oxygen partial pressure in the measurement-object gas outside of the sensor, the operation timings of the sensor cell 83 and the reference gas regulation pump cell 90 are adjusted in advance such that the variable power supply 92 does not supply the control current Ip3. This causes the oxygen pump-in operation of the reference gas regulation pump cell 90 not to interfere with the operation of the sensor cell 83.

The following gives the correspondence relationship between the components of the embodiment and the components of the invention. The first substrate layer 1, the second substrate layer 2, the third substrate layer 3, the first solid electrolyte layer 4, the spacer layer 5 and the second solid electrolyte layer 6 of the embodiment correspond to the layered body of the invention. The reference gas introducing space 43 corresponds to the reference gas introducing space. The reference electrode 42 corresponds to the reference electrode, and the measurement electrode 44 corresponds to the measurement electrode. The outer pump electrode 23 corresponds to the measurement-object gas side electrode. The measurement pump cell 41 corresponds to the detecting device. The reference gas regulation pump cell 90 and the variable power supply 92 correspond to the reference gas adjusting device. The outer pump electrode 23 corresponds to the outer electrode.

In the gas sensor 100 of the embodiment described above, oxygen is pumped in to the periphery of the reference electrode 42 by the flow of the control current Ip3 between the reference electrode 42 which the reference gas is introduced in and the outer pump electrode 23 which is provided to be exposed to the measurement-object gas. This compensates for reduction of the oxygen concentration in the periphery of the reference electrode 42, for example, when the measurement-object gas enters the reference gas introducing space 43. Controlling the average current density of the reference electrode 42 under the flow of the control current Ip3 to be higher than 0 $\mu A/mm^2$ and lower than 400 $\mu A/mm^2$ further suppresses deterioration of the reference electrode 42 by the flow of the control current Ip3 and thereby more effectively suppresses a change of the reference potential (potential of the reference electrode 42) in long time use. This accordingly compensates for reduction of the oxygen concentration in the periphery of the reference electrode 42 and more effectively suppresses a change of the reference potential in long time use. Part of the reference electrode 42 having the higher electric current is more likely to be deteriorated, for example, to reduce the size of the particles constituting the electrode and is more likely to increase the resistance of the reference electrode 42 in long time use. An increase in resistance of the reference electrode 42 changes the reference potential that is the potential of the reference electrode 42 and changes the electromotive force on the basis of the reference electrode 42, thus decreasing the detection accuracy of the NOx concentration in the measurement-object gas. This is different from a temporary change of the reference potential due to, for example, a decrease of the oxygen concentration in the periphery of the reference electrode 42 but is a permanent decrease in sensitivity due to deterioration of the reference electrode 42.

Controlling the average current density to be not higher than 170 $\mu A/mm^2$ further enhances the effect of suppressing a change of the reference potential due to deterioration of the reference electrode 42 described above. Additionally, by controlling the average value of the control current Ip3 to be higher than 1 $\mu A$, it is unlikely that the effect of compensating for reduction of the oxygen concentration in the periphery of the reference electrode 42 is insufficient. The outer pump electrode 23 as the measurement-object gas side electrode of the reference gas regulation pump cell 90 is provided on the outer surface of the layered body (or more specifically, on the second solid electrolyte layer 6). When the measurement-object gas side electrode is provided in the measurement-object gas flowing portion, oxygen in the measurement-object gas flowing portion is pumped in to the reference electrode 42-side and may thus affect the detection accuracy. Providing the measurement-object gas side electrode not in the measurement-object gas flowing portion but on the outer surface of the layered body suppresses the effect on the detection accuracy.

The gas sensor 100 includes the outer pump electrode 23 provided as the outer electrode on the outer surface of the layered body. The measurement pump cell 41 pumps in or pumps out oxygen via the measurement electrode 44 and the outer pump electrode 23 based on the voltage Vp2 generated between the reference electrode 42 and the measurement electrode 44 and detects the specific gas concentration in the measurement-object gas based on the electric current Ip2 during pump-in or pump-out. The outer pump electrode 23 as the outer electrode of the measurement pump cell 41 also works as the measurement-object gas side electrode of the reference gas regulation pump cell 90. This configuration reduces the total number of electrodes, compared with a configuration having an outer electrode different from a measurement-object gas side electrode.

The invention is not limited to the embodiment described above but may be implemented by a diversity of other configurations without departing from the scope of the invention.

For example, the control current Ip3 is dc current of a constant value in the above embodiment, but this is not restrictive. The control current Ip3 may be, for example, a pulse-like intermittent current. In the latter case, the average current density based on an average current in one period of pulse (time from a rise of a pulse to a rise of a next pulse) should be controlled to be higher than 0 µA/mm' and lower than 400 µA/mm². The control current Ip3 is dc current of a constant value and is electric current flowing consistently in the direction of pumping in oxygen to the periphery of the reference electrode 42 in this embodiment, but this is not restrictive. For example, in a certain time period, the control current Ip3 may flow in the direction of pumping out oxygen from the periphery of the reference electrode 42. The requirement is that the overall moving direction of oxygen in a predetermined sufficiently long time should be the direction of pumping in oxygen to the periphery of the reference electrode 42. More specifically, when a positive direction denotes the direction of the control current Ip3 to pump in oxygen to the periphery of the reference electrode 42 and a negative direction denotes the direction of the control current Ip3 to pump out oxygen from the periphery of the reference electrode 42, the time period in which the control current Ip3 flows in the positive direction is longer than the time period in which the control current Ip3 flows in the negative direction in the predetermined sufficiently long time. In other words, the requirement is that the average value of the control current Ip3 in the predetermined sufficiently long time should be a value in the positive direction. Even when the control current Ip3 flows in the negative direction in some time period, this compensate for reduction of the oxygen concentration in the periphery of the reference electrode 42. The control current Ip3 may have a waveform by summation of a dc component and an ac component. In this application, as long as the dc component is electric current in the positive direction, the overall moving direction of oxygen in a predetermined sufficiently long time (for example, time period of not shorter than one period of the ac component) is the direction of pumping in oxygen to the periphery of the reference electrode 42.

The outer pump electrode 23 as the outer electrode of the measurement pump cell 41 also serves as the measurement-object gas side electrode of the reference gas regulation pump cell 90 in the above embodiment, but this is not restrictive. For example, the outer electrode of the measurement pump cell 41 and the measurement-object gas side electrode of the reference gas regulation pump cell 90 may be formed separately on the outer surface of the sensor element 101. As long as the measurement-object gas side electrode of the reference gas regulation pump cell 90 is located in a region of the sensor element 101 that is exposed to the measurement-object gas, the location is not limited to the outer surface. For example, the measurement-object gas side electrode may be located in the measurement-object gas introducing space.

In the embodiment described above, the voltage Vp2 of the variable power supply 46 is controlled to maintain constant the control voltage (electromotive force) V2 detected by the measurement pump-controlling oxygen partial pressure detection sensor cell 82, and the concentration of nitrogen oxides in the measurement-object gas is calculated by using the pump current Ip2 under the control. This is, however, not restrictive, but any other suitable configuration may be employed to detect the specific gas concentration in the measurement-object gas based on the voltage between the reference electrode 42 and the measurement electrode 44. For example, the measurement electrode 44, the first solid electrolyte layer 4, the third substrate layer 3 and the reference electrode 42 may be combined to constitute an electrochemical sensor cell serving as an oxygen partial pressure detecting device. This electromotive sensor cell serves to detect an electromotive force according to a difference between the amount of oxygen produced by reduction of the NOx component in the ambient atmosphere of the measurement electrode 44 and the amount of oxygen included in the reference gas and thereby determine the concentration of the NOx component in the measurement-object gas. In this case, this electrochemical sensor cell corresponds to the detecting device of the invention.

The reference electrode 42 is formed directly on the upper surface of the third substrate layer 3 in the above embodiment, but this is not restrictive. For example, the reference electrode 4 may be formed directly on the lower surface of the first solid electrolyte layer 4.

Figure 3:
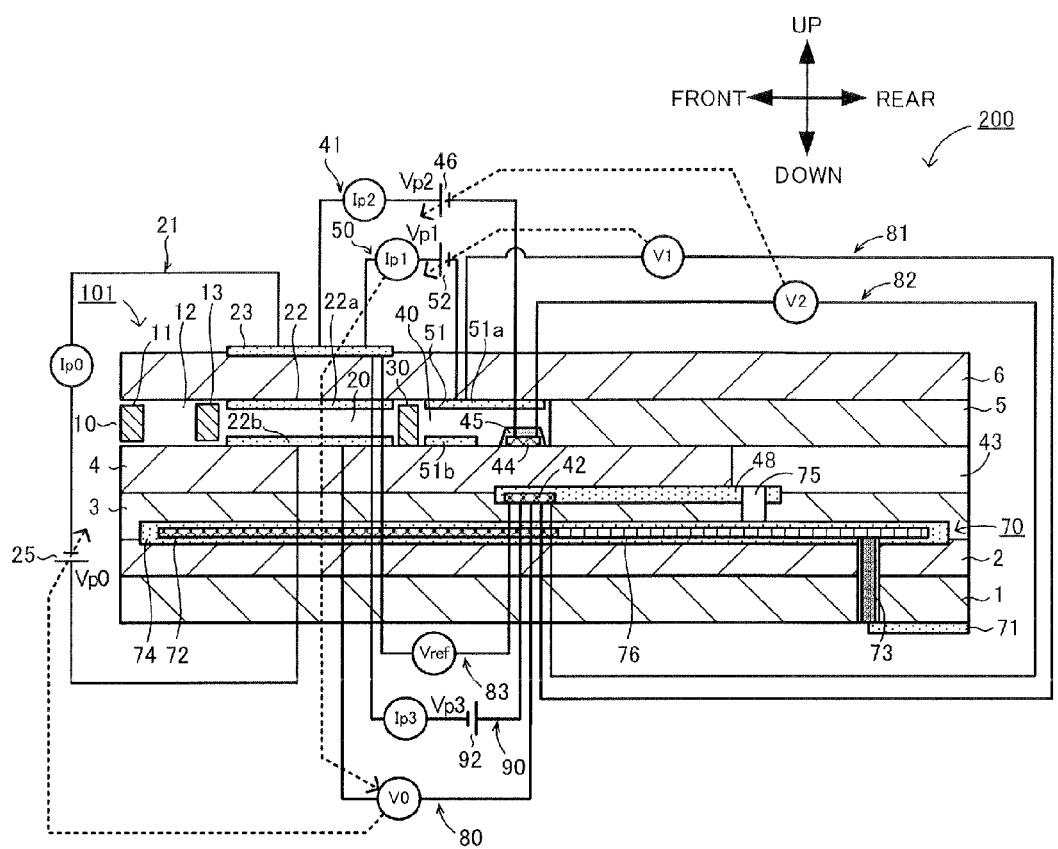
FIG. 3 is a sectional schematic diagram illustrating a sensor element 101 in a gas sensor 200 of a modification.

The sensor element 101 of the gas sensor 100 includes the first internal cavity 20, the second internal cavity 40 and the third internal cavity 61 in the above embodiment, but this is not restrictive. For example, the third internal cavity 61 may be omitted. FIG. 3 is a sectional schematic diagram illustrating a sensor element 101 of a gas sensor 200 according to this modification. As illustrated, in the gas sensor 200 of the modification, a gas inlet port 10, a first diffusion controlling portion 11, a buffer space 12, a second diffusion controlling portion 13, a first internal cavity 20, a third diffusion controlling portion 30 and a second internal cavity 40 are formed between a lower surface of a second solid electrolyte layer 6 and an upper surface of a first solid electrolyte layer 4 to be adjacent to one another and communicate with one another in this sequence. Like the fourth diffusion controlling portion 60 shown in FIG. 2, the third diffusion controlling portion 30 of the gas sensor 200 is provided in the form of one horizontally-long slit that is formed as a clearance from the lower surface of the second solid electrolyte layer 6. A measurement electrode 44 is provided on the upper surface of the first solid electrolyte layer 4 in the second internal cavity 40. The measurement electrode 44 is covered by a fourth diffusion controlling portion 45. The fourth diffusion controlling portion 45 is a membrane made of a ceramic porous material such as alumina ($Al_2O_3$). Like the fourth diffusion controlling portion 60 of the above embodiment, the fourth diffusion controlling portion 45 serves to control the amount of NOx flowing into the measurement electrode 44. The fourth diffusion controlling portion 45 also serves as a protective membrane of the measurement electrode 44. A top electrode 51a of an auxiliary pump electrode 51 is formed to cover immediately above the measurement electrode 44. Like the embodiment described above, in the gas sensor 200 of this configuration, controlling the average current density to be higher than 0 µA/mm² and lower than 400 µA/mm² ensures the effect of compensating for reduction of the oxygen concentration in the periphery of the reference electrode 42 and further suppressing a change of the reference potential in long time use.

The reference gas is the atmosphere in the above embodiment. The reference gas is, however, not limited to this embodiment but may be any gas that can be used as a standard for detection of a specific gas concentration in the measurement-object gas. For example, the space 149 may be filled with a gas with an oxygen concentration adjusted in advance to a predetermined value (>oxygen concentration in the measurement-object gas) as the reference gas.

The sensor element 101 detects the NOx concentration in the measurement-object gas in the above embodiment, but this is not restrictive. The sensor element may detect any specific gas concentration in the measurement-object gas, for example, the oxygen concentration in the measurement-object gas.

EXAMPLE

The following describes concrete examples of manufacturing gas sensors as experimental examples. Examples 1, 20, 24 and 25 are comparative examples, and Examples 2 to 19 and 21 to 23 are examples of the present invention. The invention is, however, not limited to the following examples.

Experimental Example 1

The gas sensor 100 shown in FIGS. 1 and 2 was produced by the manufacturing procedure described above as Experimental Example 1. The ceramic green sheets used for production of the sensor element 101 were formed by tape casting of a mixture of zirconia particles containing 4 mol % yttria as a stabilizing agent with an organic binder and an organic solvent. The green compacts 145a and 145b shown in FIG. 1 were compacted talc powder. The area S of the reference electrode 42 was 0.6 mm$^2$. Experimental Example 1 did not include the variable power supply 92 and had the control current Ip3 of 0 μA. The average current density of the reference electrode 42 of Experimental Example 1 was accordingly 0 μA/mm$^2$.

Experimental Example 2

A gas sensor of Experimental Example 2 was produced in the same manner as Experimental Example 1, except that Experimental Example 2 included the variable power supply 92 and regulated the voltage Vp3 to set the control current Ip3 to do current of 4 μA. The average current density of the reference electrode 42 of Experimental Example 2 was 6.7 μA/mm$^2$.

Experimental Example 3

A gas sensor of Experimental Example 3 was produced in the same manner as Experimental Example 1, except that Experimental Example 3 included the variable power supply 92 and regulated the voltage Vp3 to set the control current Ip3 to do current of 8 μA. The average current density of the reference electrode 42 of Experimental Example 3 was 13 μA/mm$^2$.

Experimental Example 4

A gas sensor of Experimental Example 4 was produced in the same manner as Experimental Example 1, except that Experimental Example 4 included the variable power supply 92 and regulated the voltage Vp3 to set the control current Ip3 to do current of 12 μA. The average current density of the reference electrode 42 of Experimental Example 4 was 20 μA/mm$^2$.

Experimental Example 5

A gas sensor of Experimental Example 5 was produced in the same manner as Experimental Example 1, except that Experimental Example 5 included the variable power supply 92 and regulated the voltage Vp3 to set the control current Ip3 to do current of 40 μA. The average current density of the reference electrode 42 of Experimental Example 5 was 67 μA/mm$^2$.

[Evaluation Relating to Change of Reference Potential Due to Penetration of Exhaust Gas]

Each of the gas sensors of Experimental Examples 1 to 5 was mounted to an exhaust gas piping of an automobile. The heater 72 was powered on to heat the sensor element 101 at a temperature of 800° C. The reference gas regulation pump cell 90 was then operated. In this state, a gasoline engine of the automobile was operated for 20 minutes under predetermined operating conditions (rotation speed of the engine was 4000 rpm, the gauge pressure of exhaust gas was 20 kPa and the λ value was 0.83). It was then determined whether the reference potential (potential of the reference electrode 42) was changed beyond a predetermined threshold value during the operation. The reference potential was measured based on the voltage Vref (voltage between the outer pump electrode 23 and the reference electrode 42) in the state that the variable power supply 92 temporarily stopped supplying the electric current Ip3. The operation of the reference gas regulation pump cell 90 supplies the control current Ip3 and pumps in oxygen, so as to compensate for reduction of the oxygen concentration in the periphery of the reference electrode 42 due to penetration of the exhaust gas into the space 149. Accordingly, a change of the reference potential beyond the predetermined threshold value means that the pump-in amount of oxygen by the reference gas regulation pump cell 90 is insufficient and the effect of compensating for reduction of the oxygen concentration is insufficient. According to the results of this test, Experimental Example 1 had a change of the reference potential beyond the threshold value at 10 minutes after the start of the engine operation. Experimental Example 2 had a change of the reference potential beyond the threshold value at 18 minutes after the start of the engine operation. With regard to Experimental Examples 3 to 5, the reference potential did not change beyond the threshold value even after elapse of 20 minutes. These results show that the effect of compensating for reduction of the oxygen concentration in the periphery of the reference electrode 42 is sufficient with regard to Experimental Examples 3 to 5 having the control current Ip3 of not lower than 8 μA.

Examples 6 to 25

Gas sensors of Experimental Examples 6 to 25 were produced in the same manner as Experimental Examples 2 to, except that the area S of the reference electrode 42, the control current Ip3 and the average current density of the reference electrode 42 were regulated as shown in Table 1. An area ratio shown in Table 1 is a value of the area S in each Experimental Example relative to the area S of the reference electrode 42 equal to 1 in Experimental Examples 1 to 5. The results of Examples 1 to 5 are also shown in Table 1.

[Evaluation Test 1]

Experimental Examples 6 to 25 were subjected to the same test as that of Experimental Examples 1 to 5 described above, and it was determined whether the reference potential (voltage Vref) was changed beyond the predetermined threshold value in 20 minutes. The results of evaluation are shown in Table 1. In Table 1, the time when the reference potential changed beyond the threshold value is shown as the result of Evaluation Test 1. In Table 1, "longer than 20 minutes" means that the reference potential did not change beyond the threshold value in 20 minutes. With regard to Experimental Examples 6 to 10 having the control current Ip3 of 1 μA, the reference potential changed beyond the threshold value at 15 minutes to 17 minutes after the start of the engine operation. This indicates that the effect of compensating for reduction of the oxygen concentration in the periphery of the reference electrode 42 is insufficient. With regard to Experimental Examples 11 to 15 having the control current Ip3 of 4 μA, the reference potential changed beyond the threshold value at 18 to 19 minutes after the start of the engine operation in some examples and the reference potential did not change beyond the threshold value after elapse of 20 minutes in one example. With regard to Experimental Examples 16 to 25, the reference potential did not change beyond the threshold value after elapse of 20 minutes in all examples. These results show that it is unlikely that the effect of compensating for reduction of the oxygen concentration in the periphery of the reference electrode 42 is insufficient with regard to Experimental Examples 2 to 5 and 11 to 25 having the control current Ip3 of higher than 1 μA.

[Evaluation Test 2]

Figure 4:
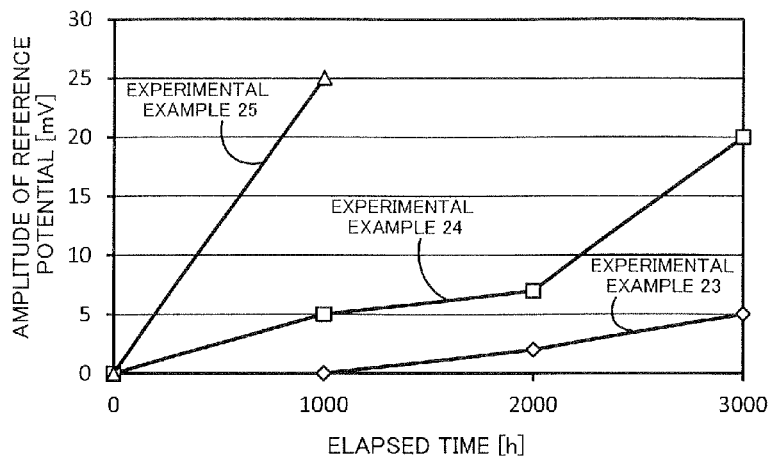
FIG. 4 is a graph showing variations in amplitude of reference potential against time elapsed with regard to Experimental Examples 23 to 25.

Experimental Examples 2 to 25 were subjected to a durability test using a diesel engine, and the degree of deterioration of the reference electrode was evaluated. More specifically, the test was performed as described below. Each of the gas sensors of Experimental Examples 2 to 25 was mounted to an exhaust gas piping of an automobile. The heater 72 was powered on to heat the sensor element 101 at a temperature of 800° C. The reference gas regulation pump cell 90 was then operated. In this state, an operation pattern of forty minutes in the range of the engine rotation speed of 1500 to 3500 rpm and the load torque of 0 to 350 N·m was repeated until elapse of 3000 hours. The gas temperature was 200 to 600° C., and the NOx concentration was 0 to 1500 ppm. Each of the gas sensors was evaluated for any control failure until elapse of 3000 hours. The results of evaluation are shown in Table 1. In Table 1, the time when a control failure occurred is shown as the result of Evaluation Test 2. In Table 1, "longer than 3000 hours" means that no control failure occurred until elapse of 3000 hours. With regard to Experimental Examples 20, 24 and 25 having the average current density of not lower than 400 μA/mm$^2$, control failure occurred before elapse of 3000 hours. The higher average current density was likely to shorten the time before the occurrence of control failure. With regard to Experimental Examples 23, 24 and 25, the variable power supply 92 temporarily stopped supplying the electric current Ip3 and the gas sensor was demounted from the exhaust gas piping to be kept in the air atmosphere. The reference potential was measured based on the voltage Vref (voltage between the outer pump electrode 23 and the reference electrode 42) in this state, and a variation (amplitude) of reference potential was measured. FIG. 4 is a graph showing variations in amplitude of reference potential against time elapsed with regard to Experimental Examples 23 to 25. As illustrated, Experimental Examples 24 and 25 with control failure occurring before elapse of 3000 hours had relatively large variations (amplitudes) in reference potential of 20 mV and 25 mV. Experimental Example 23 with no control failure occurring after elapse of 3000 hours had, on the other hand, a small variation in reference potential of 5 mV at the time of elapse of 3000 hours. These results show that controlling the average current density to be lower than 400 μA/mm$^2$ suppresses a change of the reference potential in long time use.

TABLE 1

| | Area S [mm$^2$] | Area Ratio | Control Current Ip3 [μ A] | Average Current Density [μA/mm$^2$] | Evaluation Test 1 ※1 | Evaluation Test 2 ※2 |
|---|---|---|---|---|---|---|
| Experimental Example 1 | 0.6 | 1.00 | 0 | 0 | 10 minutes | — |
| Experimental Example 2 | 0.6 | 1.00 | 4 | 6.7 | 18 minutes | longer than 3000 hours |
| Experimental Example 3 | 0.6 | 1.00 | 8 | 13 | longer than 20 minutes | longer than 3000 hours |
| Experimental Example 4 | 0.6 | 1.00 | 12 | 20 | longer than 20 minutes | longer than 3000 hours |
| Experimental Example 5 | 0.6 | 1.00 | 40 | 67 | longer than 20 minutes | longer than 3000 hours |
| Experimental Example 6 | 4 | 6.67 | 1 | 0.3 | 15 minutes | longer than 3000 hours |
| Experimental Example 7 | 2 | 3.33 | 1 | 0.5 | 17 minutes | longer than 3000 hours |
| Experimental Example 8 | 0.6 | 1.00 | 1 | 1.7 | 15 minutes | longer than 3000 hours |
| Experimental Example 9 | 0.25 | 0.42 | 1 | 4 | 16 minutes | longer than 3000 hours |
| Experimental Example 10 | 0.04 | 0.07 | 1 | 25 | 15 minutes | longer than 3000 hours |
| Experimental Example 11 | 4 | 6.67 | 4 | 1 | longer than 20 minutes | longer than 3000 hours |
| Experimental Example 12 | 2 | 3.33 | 4 | 2 | 18 minutes | longer than 3000 hours |
| Experimental Example 13 | 0.6 | 1.00 | 4 | 6.7 | 19 minutes | longer than 3000 hours |

TABLE 1-continued

|  | Area S [mm$^2$] | Area Ratio | Control Current Ip3 [μA] | Average Current Density [μA/mm$^2$] | Evaluation Test 1 ※1 | Evaluation Test 2 ※2 |
|---|---|---|---|---|---|---|
| Experimental Example 14 | 0.25 | 0.42 | 4 | 16 | 19 minutes | longer than 3000 hours |
| Experimental Example 15 | 0.04 | 0.07 | 4 | 100 | 18 minutes | longer than 3000 hours |
| Experimental Example 16 | 4 | 6.67 | 20 | 5 | longer than 20 minutes | longer than 3000 hours |
| Experimental Example 17 | 2 | 3.33 | 20 | 10 | longer than 20 minutes | longer than 3000 hours |
| Experimental Example 18 | 0.6 | 1.00 | 20 | 33 | longer than 20 minutes | longer than 3000 hours |
| Experimental Example 19 | 0.25 | 0.42 | 20 | 80 | longer than 20 minutes | longer than 3000 hours |
| Experimental Example 20 | 0.04 | 0.07 | 20 | 500 | longer than 20 minutes | 3000 hours |
| Experimental Example 21 | 4 | 6.67 | 100 | 25 | longer than 20 minutes | longer than 3000 hours |
| Experimental Example 22 | 2 | 3.33 | 100 | 50 | longer than 20 minutes | longer than 3000 hours |
| Experimental Example 23 | 0.6 | 1.00 | 100 | 167 | longer than 20 minutes | longer than 3000 hours |
| Experimental Example 24 | 0.25 | 0.42 | 100 | 400 | longer than 20 minutes | 3000 hours |
| Experimental Example 25 | 0.04 | 0.07 | 100 | 2500 | longer than 20 minutes | 1000 hours |

Figure 5:
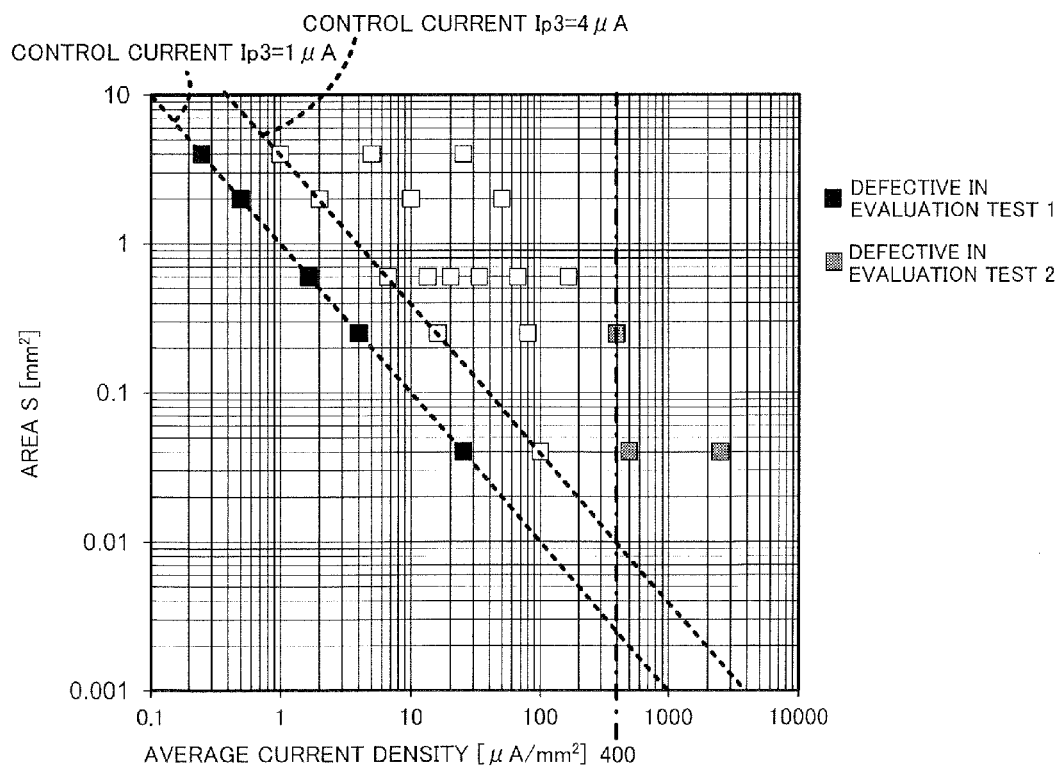
FIG. 5 is a graph showing an area S plotted against current density with regard to Experimental Examples 2 to 25.
Figure 6:
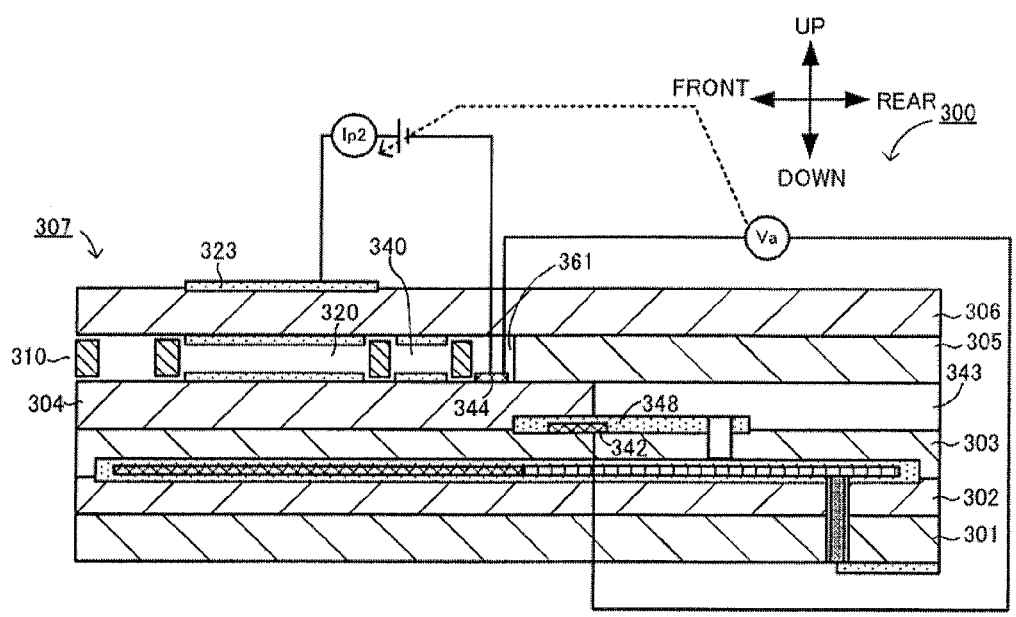
FIG. 6 is a sectional schematic diagram illustrating a prior art gas sensor 300.

※1 the time when the pump-in amount of oxygen by the reference gas regulation pump cell is insufficient in case the sensor element is exposed to exhaust gas
※2 the time when a control failure occurred in case the sensor element is exposed to exhaust gas FIG. 5 is a graph showing an area S plotted against average current density with regard to Experimental Examples 2 to 25. In FIG. 5, the results of Experimental Examples 6 to 10 determined as defective in Evaluation Test 1 and the results of Experimental Examples 20, 24 and 25 determined as defective in Evaluation Test 2 are shown distinctively.

As shown in Table 1 and FIG. 5, controlling the average current density to be lower than 400 μA/mm$^2$ more effectively suppresses a change of the reference potential in long time use. By controlling the control current Ip3 to be higher than 1 μA, it is unlikely that the effect of compensating for reduction of the oxygen concentration in the periphery of the reference electrode is insufficient.

The present application claims priority from Japanese Patent Application No. 2014-072928 filed on Mar. 31, 2014, and Japanese Patent Application No. 2015-063962 filed on Mar. 26, 2015, the entire contents of which are incorporated herein by reference.

What is claimed is:

1. A gas sensor comprising:
   a layered body that is formed by stacking a plurality of oxygen ion-conductive solid electrolyte layers, and that includes, formed therein, a measurement-object gas flowing portion in which a measurement object gas is introduced and flowed and a reference gas introducing space in which a reference gas used as a standard for detection of a specific gas concentration in the measurement-object gas is introduced,
   a reference electrode that is formed inside of the layered body, and that receives the reference gas introduced therein via the reference gas introducing space,
   a measurement electrode provided on an inner peripheral surface of the measurement-object gas flowing portion,
   a measurement-object gas side electrode provided in a region of the layered body that is exposed to the measurement-object gas,
   a detecting device that detects the specific gas concentration in the measurement-object gas based on an electromotive force generated between the reference electrode and the measurement electrode, and
   a reference gas adjusting device that pumps in oxygen to a periphery of the reference electrode by a flow of control current between the reference electrode and the measurement-object gas side electrode,
   wherein an average current density of the reference electrode under the flow of the control current is higher than 0 μA/mm$^2$ and lower than 400 μA/mm$^2$.

2. The gas sensor according to claim 1, wherein the average current density is not higher than 170 μA/mm$^2$.

3. The gas sensor according to claim 1, wherein an average value of the control current is higher than 1 μA.

4. The gas sensor according to claim 1, wherein the measurement-object gas side electrode is provided on an outer surface of the layered body.

5. The gas sensor according to claim 1, comprising an outer electrode provided on an outer surface of the layered body,
   wherein the detecting device pumps out or pumps in oxygen via the measurement electrode and the outer electrode based on an electromotive force generated between the reference electrode and the measurement electrode and detects the specific gas concentration in the measurement-object gas based on an electric current during pump-out or pump-in.

6. The gas sensor according to claim 5, wherein the outer electrode also serves as the measurement-object gas side electrode.

* * * * *